(12) United States Patent
Farrell et al.

(10) Patent No.: US 11,730,918 B2
(45) Date of Patent: Aug. 22, 2023

(54) CATHETER ASSEMBLY WITH ANTI-STAINING HYDRATION FLUID

(71) Applicant: Hollister Incorportated, Libertyville, IL (US)

(72) Inventors: David J. Farrell, Ballina (IE); Satwinder S. Panesar, Foxford (IE); Vincent Naughton, Sligo (IE); Daniel E. O'Brien, Calry (IE)

(73) Assignee: Hollister Incorporated, Libertyville, IL (US)

( * ) Notice: Subject to any disclaimer, the term of this patent is extended or adjusted under 35 U.S.C. 154(b) by 783 days.

(21) Appl. No.: 16/487,369

(22) PCT Filed: Feb. 20, 2018

(86) PCT No.: PCT/US2018/018780
§ 371 (c)(1),
(2) Date: Aug. 20, 2019

(87) PCT Pub. No.: WO2018/156502
PCT Pub. Date: Aug. 30, 2018

(65) Prior Publication Data
US 2020/0054795 A1    Feb. 20, 2020

Related U.S. Application Data

(60) Provisional application No. 62/461,730, filed on Feb. 21, 2017, provisional application No. 62/545,730, filed on Aug. 15, 2017.

(51) Int. Cl.
*B65D 83/10* (2006.01)
*A61M 25/00* (2006.01)
(Continued)

(52) U.S. Cl.
CPC ....... *A61M 25/0017* (2013.01); *A61L 29/085* (2013.01); *A61L 29/14* (2013.01);
(Continued)

(58) Field of Classification Search
CPC ............ A61M 25/0017; A61M 25/002; A61M 25/0045; A61M 2025/0046; A61L 2202/24; A61L 2/08
(Continued)

(56) References Cited

U.S. PATENT DOCUMENTS

5,876,663 A    3/1999 Laroussi
6,059,107 A *  5/2000 Nøsted ............. A61M 25/0017
206/364

(Continued)

FOREIGN PATENT DOCUMENTS

CN    104474583 B    2/2017
EP    1252898 A2    10/2002
(Continued)

OTHER PUBLICATIONS

International Search Report and Written Opinion of the International Searching Authority dated Sep. 28, 2018 for International Application No. PCT/US2018/018780.
(Continued)

*Primary Examiner* — Luan K Bui
(74) *Attorney, Agent, or Firm* — Cook Alex Ltd.

(57) ABSTRACT

Gels that release fluid and assemblies containing the same.

27 Claims, 1 Drawing Sheet

(51) Int. Cl.
*A61L 29/08* (2006.01)
*A61L 29/14* (2006.01)

(52) U.S. Cl.
CPC ......... *A61L 29/145* (2013.01); *A61M 25/002* (2013.01); *A61M 25/0045* (2013.01); *A61L 2202/24* (2013.01); *A61M 2025/0046* (2013.01)

(58) Field of Classification Search
USPC ......... 206/364–365, 438, 570–572; 604/172, 604/265, 544
See application file for complete search history.

(56) References Cited

U.S. PATENT DOCUMENTS

| | | | |
|---|---|---|---|
| 6,634,498 B2 * | 10/2003 | Kayer | A61L 29/085 206/364 |
| 6,848,574 B1 * | 2/2005 | Israelsson | B65D 75/32 206/364 |
| 6,923,936 B2 | 8/2005 | Swanson et al. | |
| 6,986,868 B2 | 1/2006 | Madsen | |
| 7,282,165 B2 | 10/2007 | Williams et al. | |
| 7,833,475 B2 * | 11/2010 | Madsen | A61L 2/081 422/23 |
| 8,127,922 B2 * | 3/2012 | Nordholm | A61M 25/0111 604/265 |
| 8,133,435 B2 | 3/2012 | Reynolds et al. | |
| 8,267,919 B2 * | 9/2012 | Utas | A61M 25/002 604/317 |
| 8,703,048 B2 | 4/2014 | Nielsen et al. | |
| 8,998,882 B2 | 4/2015 | Knapp et al. | |
| 9,138,510 B2 | 9/2015 | Madsen | |
| 9,220,866 B2 | 12/2015 | Van Groningen et al. | |
| 2003/0065292 A1 | 4/2003 | Darouiche et al. | |
| 2003/0136426 A1 | 7/2003 | Aoyagi | |
| 2004/0256264 A1 | 12/2004 | Israelsson et al. | |
| 2005/0070882 A1 * | 3/2005 | McBride | A61M 25/002 206/571 |
| 2005/0109648 A1 * | 5/2005 | Kerzman | A61M 25/0111 206/364 |
| 2005/0214443 A1 * | 9/2005 | Madsen | A61L 2/08 427/2.24 |
| 2006/0263404 A1 * | 11/2006 | Nielsen | A61M 25/0045 424/422 |
| 2008/0152698 A1 | 6/2008 | Effing et al. | |
| 2009/0240214 A1 * | 9/2009 | Conway | A61M 25/002 206/572 |
| 2010/0055153 A1 | 3/2010 | Majmudar | |
| 2011/0058982 A1 * | 3/2011 | Kaneko | A61L 2/087 422/22 |
| 2011/0190392 A1 | 8/2011 | Najafi et al. | |
| 2012/0316515 A1 | 12/2012 | Terry | |
| 2013/0186778 A1 * | 7/2013 | Terry | A61F 2/042 206/210 |
| 2014/0190846 A1 | 7/2014 | Belt | |
| 2014/0249489 A1 | 9/2014 | Madsen | |
| 2014/0271351 A1 | 9/2014 | Nielsen et al. | |
| 2015/0238726 A1 | 8/2015 | Terry | |
| 2015/0335854 A1 * | 11/2015 | Dvärsäter | A61M 25/002 206/364 |
| 2017/0340857 A1 * | 11/2017 | Ryan | A61M 25/0045 |
| 2018/0021481 A1 * | 1/2018 | Yin | A61L 29/085 206/364 |
| 2021/0178026 A1 | 6/2021 | Farrell et al. | |

FOREIGN PATENT DOCUMENTS

| | | |
|---|---|---|
| EP | 1131112 B1 | 2/2003 |
| EP | 1175355 B1 | 9/2006 |
| EP | 1961429 A2 | 8/2008 |
| EP | 2060296 A1 | 5/2009 |
| EP | 1312385 B2 | 10/2009 |
| EP | 1888127 B1 | 1/2010 |
| EP | 2695636 A1 | 2/2014 |
| EP | 2065061 B1 | 3/2015 |
| EP | 1723980 B2 | 6/2016 |
| EP | 2515988 B1 | 7/2016 |
| EP | 3248620 A1 | 11/2017 |
| WO | WO 00/30696 A1 | 6/2000 |
| WO | WO 00/47494 A1 | 8/2000 |
| WO | WO 02/100455 A2 | 12/2002 |
| WO | WO 2006/117372 A1 | 11/2006 |
| WO | WO 2011/109393 A1 | 9/2011 |
| WO | WO 2014/165046 A1 | 10/2014 |
| WO | WO 2015/066238 A2 | 5/2015 |
| WO | WO 2016/033234 A1 | 3/2016 |

OTHER PUBLICATIONS

Partial European Search Report dated Jul. 28, 2020, from EP Appl. No. 20178588.8.
Haji-Saeid et al., "Radiation Treatment for Sterilization of Packaging Materials", Radiation Physics and Chemistry, 2007, pp. 1535-1541, vol. 76.
Kondyurina et al., "Urinary catheter with polyurethane coating modified by ion implantation", Nuclear Instruments and Methods in Physics Research B, 2015, pp. 39-46, vol. 342.
Vahr et al., "Catheterisation: Urethral intermittent in adults", European Association of Urology Nurses, 2013.
Zainuddin et al., "Radiation-induced degradation and crosslinking of poly(ethylene oxide) in solid state", Journal of Radioanalytical and Nuclear Chemistry, 2002, pp. 339-344, vol. 253, No. 3.
Bueno et al., "Synthesis and swelling behavior of xanthan-based hydrogels", Elsevier, Carbohydrate Polymers, vol. 92, pp. 1091-1099 (2013).
Non-Final Office Action dated Nov. 10, 2022 for U.S. Appl. No. 16/760,183.
Final Office Action for U.S. Appl. No. 16/760,183 dated Mar. 30, 2023.

* cited by examiner

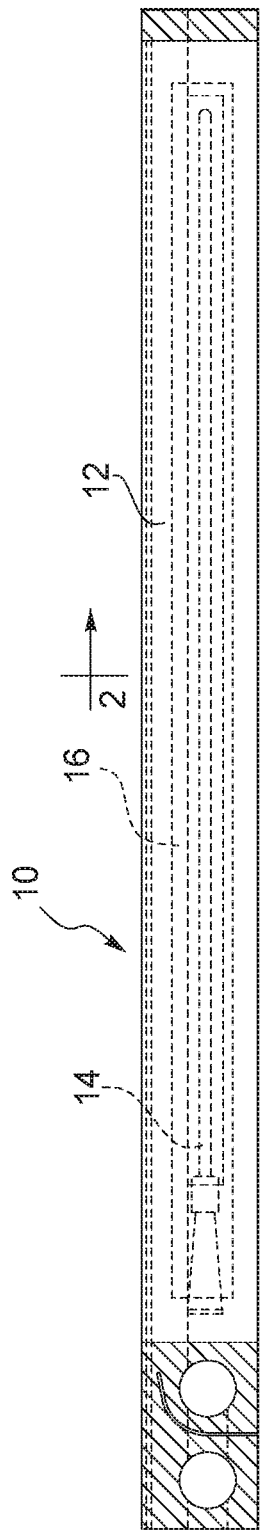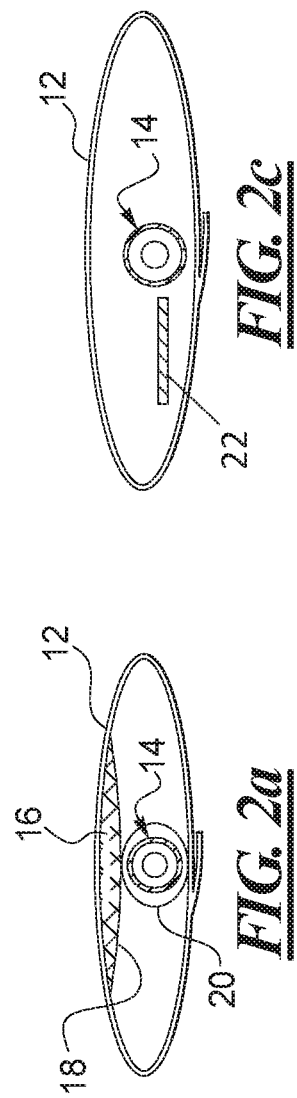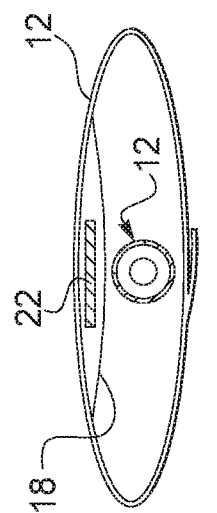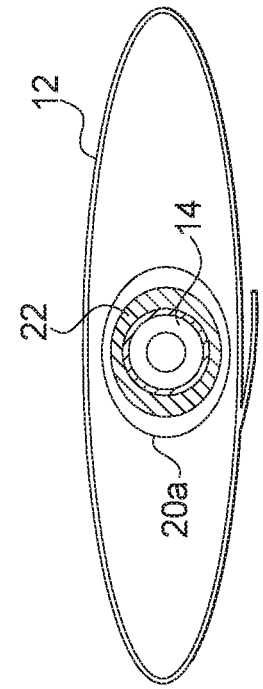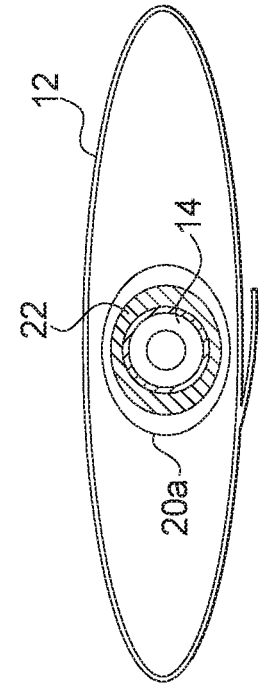

CATHETER ASSEMBLY WITH ANTI-STAINING HYDRATION FLUID

RELATED APPLICATION

The present application is the U.S. National Stage Application of PCT Application No. PCT/US2018/018780, filed Feb. 20, 2018, which claims the benefit and priority of U.S. Provisional Patent Application No. 62/461,730, filed Feb. 21, 2017, and U.S. Provisional Patent Application No. 62/545,730, filed Aug. 15, 2017, all of which are hereby incorporated herein by reference.

TECHNICAL FIELD

The present disclosure generally relates to hydration gels that release fluid for hydrating or wetting materials, such as hydrophilic materials, and more particularly, to radiation activated hydration gels that contain a fluid which is released from a gel upon exposing the gel to radiation. The present disclosure also generally relates to assemblies that include products having a material to be wetted or hydrated or a material to be stored in a wet state and a fluid releasing hydrogel. The present disclosure also generally relates to methods for radiation sterilization of materials, such as hydrophilic materials.

BACKGROUND

One method of sterilization includes exposing an item or product to radiation to kill the microbes and sterilize the item/product. There are items/products wherein the conditions under which the radiation sterilization occurs can cause damage to the items/products. For example, there are certain items that are required to be radiation sterilized in dry or substantially dry conditions. If such items are radiation sterilized in a wet or hydrated condition, the exposure to radiation may lessen one or more qualities of the item or will damage the item. For example, some types of hydrophilic materials may become damaged by exposure to sterilizing radiation while the hydrophilic materials are in a hydrated state.

It is known to coat medical devices, such as urinary catheters, with a hydrophilic coating. When the hydrophilic coating is wetted or hydrated with a wetting fluid, such as water, it becomes extremely lubricous which eases introduction of the device into the body and aids in reducing pain and discomfort associated with such introduction.

In some applications, the hydrophilically coated medical device is provided in a "dry" state wherein the user is required to wet the hydrophilic coating with a wetting fluid immediately prior to insertion into the body. In other applications, it is desirable to provide a hydrophilically coated medical device that is in a ready-to-use condition right out of the package. In the field of urinary catheters, a hydrophilically coated catheter may be provided in a catheter package wherein the catheter is stored in the package in contact with water so that the hydrophilic coating is wetted within the package and the catheter is ready for use right out of the package.

For various reasons, including but not limited to efficiency, effectiveness and cost, it is desirable to radiation sterilize packaged medical device assemblies. In some instances, the hydrophilically coated medical device and water are placed in the package and the package is sealed. After the package is sealed, the package having the hydrophilically coated medical device and water therein is exposed to radiation, such as gamma or E-Beam radiation, to sterilize the medical device. It has been found, however, that sterilization of hydrophilic coatings in the hydrated state or while in contact with a wetting fluid can result in degradation of the coating or excessive crosslinking of the coating which can lead to an increase of coefficient of friction (decrease in lubricity) of the coating and/or cause instability of coating which may result in the coating undesirably detaching from the medical device prior to or during use.

Therefore, there remains a need for sterilized ready-to-use hydrophilic medical devices and methods of sterilizing hydrophilic medical devices.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an assembly includes a device and a radiation activated fluid releasing gel containing a fluid, such as liquid. The liquid may be, for example, liquid water or a solution containing water. In one embodiment, the fluid is a hydration fluid that hydrates a material of the device. Prior to exposing the assembly to sterilizing radiation, the fluid releasing gel retains the fluid and prevents or substantially prevents the fluid from contacting the device. As such, prior to radiation, the device is in a dry or substantially dry state. When the device includes a hydrophilic material, the hydrophilic material may be in non-hydrated or non-fully hydrated state. Because of this, the device may be irradiated in a dry state and/or the irradiation may begin while the device is not in contact with the fluid contained in fluid releasing gel. Upon exposure to radiation, the gel releases the fluid, which contacts the device, thereby resulting in a sterilized device.

In another aspect, a method of sterilizing a device including placing a device and a gel containing a fluid within a package, and exposing the device and gel to sterilizing radiation, wherein the gel is activated or triggered to release the fluid, such as liquid water or a solution containing water, upon exposure to the radiation.

BRIEF DESCRIPTION OF FIGURES

FIG. 1 is a plan view of a catheter assembly in accordance with the present disclosure;

FIG. 2a is a cross-sectional view of one embodiment of the catheter assembly of FIG. 1 taken along line 2-2;

FIG. 2b is a cross-sectional view of another embodiment of the catheter assembly of FIG. 1 taken along line 2-2;

FIG. 2c is a cross-sectional view of another embodiment of the catheter assembly of FIG. 1 taken along line 2-2; and FIG. 2d is a cross-sectional view of another embodiment of the catheter assembly of FIG. 1 taken along line 2-2.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure discloses gels that are activated to release fluids and assemblies that include the same. The fluids may be, for example, liquid water or a solution containing liquid water. The gels may be radiation activated in that when the gel is exposed to radiation, such as sterilizing E-beam or gamma radiation, the gel degrades or breaks down, thereby releasing fluid. Such gels may be used in any assembly that requires the liquid fluid to remain within the gel prior to being exposed to radiation. For example, hydration gels may be used in an assembly that includes a device and a hydration gel wherein the hydration gel retains fluids and keeps the fluid from contacting the device until the hydration gel is activated or broken down by exposure to radiation to release the fluid.

The gels disclosed herein may be used in any field or industry, e.g. consumer products, medical products, industrial products, food products, textiles etc. The gels may be employed in any package or situation that requires active hydration of an item after radiation. In one example, the fluid releasing gels may be used with any item that expands in dimensions upon contact with a liquid. For example, a sponge may be in a compact configuration when in a dry state and in an expanded configuration when in a wet state. The sponge may be packaged with a fluid releasing gel in the dry state. After being exposed to radiation, the gel releases fluid that wets the sponge, thereby expanding the sponge.

In another example, the gels may be used in medical device assemblies. The medical device may include any natural or synthetic material wherein the material is required to be separated from the fluid of the gel until the gel releases the fluid. Such materials may include polymers, metals, organic material, tissue, etc. In one embodiment, such gels may be used to hydrate hydrophilic materials during and/or after exposure to sterilizing radiation. Such medical devices may include any medical device that utilizes a lubricious hydrophilic material, including but not limited to, urinary catheters, endoscopes, anal catheters, vascular catheters, etc. The lubricious hydrophilic material may be a hydrophilic coating on the device.

In one embodiment, the assembly includes a hydrophilically coated medical device (such as a urinary catheter or anal catheter) and a hydration gel containing a fluid, such as a hydration fluid, which may be liquid water or a solution containing water. Prior to releasing the fluid, the hydration gel retains the fluid, thereby preventing or substantially preventing the fluid from hydrating the hydrophilic coating. That is, the hydrophilic coating is in a dry (non-hydrated) or a non-fully hydrated state. The medical assembly is then exposed to sterilizing radiation with the hydrophilic coating in the dry or non-fully hydrated state. Upon exposure radiation, the hydration gel releases the fluid. The released fluid hydrates the hydrophilic coating on the medical device, rending the hydrophilic coating lubricous and ready for use, and resulting in a sterilized ready-to-use medical device. In hydrating the hydrophilic coating, the fluid may be in direct liquid contact with the hydrophilic coating and/or the released liquid fluid may produce a vapor that hydrates the hydrophilic coating.

The hydration gel may be any fluid containing gel that is activated to release the fluid upon being exposed to radiation. In one embodiment, when the gel is exposed to radiation, the gel degrades or breaks down, thereby releasing the fluid. For example, upon exposure to radiation, the viscosity of the gel may be lowered or the gel may liquefy, thereby releasing the fluid.

In one embodiment, the gels may include a polymeric mixture and an amount of fluid. For example, the gel may be a water soluble polymer based hydrogel, such as a saccharide based hydrogel. In one embodiment, the hydrogel may be a polysaccharide based gel which includes a polysaccharide and a concentration of fluid. The gel may be, for example, various hydrocolloids that form a gel in the presence of water. Such hydrocolloids include but are not limited to gellan gum, high acyl gellan gum, low acyl gellan gum, xanthan gum, deacetylated xanthan gum, depyruvated xanthan gum, galactomannans, glucomannans, and combinations thereof and a concentration of fluid. In one embodiment, the gel is a thermoreversible gel that is radiation degradable, such as a xanthan gum based gel. The concentration of the polymeric mixture of the gel may be between about 60 wt % and about 0.1 wt %. In one embodiment, the concentration of the polymeric mixture may be between about 0.1 wt % and about 5 wt % or between about 1 wt % and about 2 wt %, or between about 1.25 wt % and about 1.75 wt %.

The concentration of the fluid in the gel may be between about 40 wt % and about 99.9 wt %. In one embodiment, the concentration of the fluid in the gel is about 98 wt % with difference being the polymeric mixture and optional additives. In one embodiment, the hydrogel may include a polymeric mixture in an amount of between about 1 wt % and about 2 wt % and fluid in an amount of between about 98 wt % and about 99 wt %.

The fluid may be any liquid fluid. In one embodiment, the fluid is a liquid fluid that hydrates the hydrophilic coating by direct liquid contact and/or by donating a vapor. In one embodiment, the fluid may include water or a solution containing water. The fluid may also be a saline solution. The fluid and/or the gel may also include additives, which may be functional components of the fluid, the gel and/or both. Such additives may include but are not limited to, ionic compounds, plasticizers, alcohols, osmolality increasing agent, antibiotics, etc. For example, the ionic compounds may be those that include sodium, potassium, calcium and/or magnesium. Furthermore, the additives may be outside of and adjacent to the gel wherein the additives mix with the fluid when the fluid is released from the gel. In another embodiment, the assembly may include two or more gels wherein each gel has different components, such as different fluids, concentration of fluids and/or additives.

The hydrogel may include one or more additives which serve as hydrogel stabilizing or strengthening agents, such as simple polyols (such as glycerol), polyethers (such as Polyethylene glycol) and/or carboxylic acid (such as citric acid, polycarboxylic acid or salts thereof). For example, the additives may be one or more of glycerol, Polyethylene glycol, Xylotol, sodium citrate, tartaric acid, oxalic acid, poly(acrylic acid and poly(acrylic acid) salt (such as sodium). The polyols and polyethers may have molecular weights between about 100 Mw and about 600 Mw. In one embodiment, the hydrogel may include glycerol in a concentration of less than about 5 wt % or in less than about 2 wt %. For example, the glycerol concentration may be between about 0.1 wt % and about 5 wt %, or between about 0.5 wt % and about 2 wt %, or between about 0.1 wt % and about 1 wt % or between about 0.25 wt % and about 0.5 wt %. In another embodiment, the hydrogel may include polyethylene glycol in a concentration a concentration of less than about 5 wt % or in less than about 2 wt %. In addition to glycerol and polyethylene, or in the alternative to these, the hydrogel may include citric acid. The citric acid may be in the amount between about 0.01 wt % and about 2 wt %, or between about 0.01 wt % and about 0.5 wt % or between about 0.05 wt % and about 0.1 wt %.

It is desirable for the amount of stabilizing agents to be sufficient to stabilize the gel but to also allow the hydration gel to breakdown or release the fluid upon exposure to radiation, such as sterilizing gamma or E-beam radiation. If the amount of stabilizing agent included in the hydration gel is too great, the hydration gel may not sufficiently breakdown or release the fluid.

Some fluids for hydrating hydrophilic catheters have been known to cause stains when the fluid is spilled or otherwise comes into contact with clothing. While some hydrophilic catheter packages are designed to reduce the risk of fluid spillage, accidents still occur, which can leave unsightly or embarrassing stains on the user's clothing. Surprisingly, with the addition of additives to the hydration gels, the fluid released from the hydration gel does not stain or results in reduced staining of clothes.

The gels may include an anti-staining agent(s) that may mask or act as a clarifying agent. Such anti-staining agents may include the same simple polyols (such as glycerol), polyethers (such as polyethylene glycol) and/or carboxylic acid (such as citric acid) that also act as stabilizing/strengthening agents. The anti-staining agents can result in no staining, reduced staining and/or the formation of a transparent film or residue on the clothing. In one embodiment, a hydration gel includes a polymeric composition, such as gellan gum, a stabilizing and/or anti-staining agent such as (glycerol, PEG and/or citric acid). For example, the hydration gel may include between about 1 wt % and about 2 wt % of the polymeric composition, between about 0.1 wt % and about 2 wt % stabilizing and/or anti-staining agents (which may be the same of different agents), and between about 96 wt % to about 98.9 wt % fluid (such as water or saline). In another embodiment, the anti-staining agents may be contained in the above concentrations in a wetting fluid for wetting or hydrating a hydrophilic catheter. Such anti-staining wetting fluid may be contained in a gel or it be placed directly into a package without the use of gel. For example, such anti-staining wetting fluid may be placed directly into the package with a hydrophilic catheter wherein the wetting fluid is in direct contact with the catheter or at some point in time brought into direct contact with the catheter.

One embodiment of a medical device assembly includes a package containing a hydrophilically coated medical device (such as a urinary or anal catheter) and a gel containing a fluid wherein the gel releases the fluid to hydrate the hydrophilically coating of the medical device in the package. The gel may be a radiation activated hydration gel that releases the fluid upon exposure to radiation, such as gamma or E-beam sterilizing radiation. After, sterilization, the medical device within the package is sterilized and in a ready-to-use hydrated state. With the medical device in a ready-to-use state, the package is distributed to the user wherein the medical device is ready to use when the package is opened by the user.

A gel and the device may be configured within the package in any variety of manners. For example, the gel may serve as a reservoir of fluid that retains the fluid until the gel releases the fluid, by for example, degradation of the gel from exposure to radiation. The gel may or may not be in contact with the device prior to release of the fluid. The device may be, for example, a medical device. In one embodiment, the gel at least partially covers or is partially spread over the device. Alternatively, the gel may substantially cover or be substantially spread over the device. For example, when the device includes a hydrophilic coating, the gel may at least partially or substantially cover of at least the hydrophilic coating of the medical device. In another embodiment, the gel and the device may be unconstrained relative to one another within the package, wherein the gel and device are free to move about relative to one another. In yet another embodiment, the gel may be confined within a section of the package or in isolation relative to the device. For example, the gel may be separated from the device by a gas permeable barrier, which in one embodiment also may be a liquid impermeable barrier. In such an embodiment, when the liquid fluid is released, the liquid fluid provides a vapor that permeates through the barrier and hydrates the hydrophilic coating. Another embodiment may include placing the gel and hydrophilic catheter, such as a urinary or anal catheter, within a liquid impermeable barrier such that it can provide more efficient direct hydration of the hydrophilic material of the catheter.

In one method of sterilizing a medical device containing a hydrophilic material, such as a hydrophilically coated urinary or anal catheter, the medical device and a hydration gel are placed within a package. The package may or may not be sealed. The hydration gel may be placed in the package in any suitable manner. For example, during formation of the hydration gel, the gel may be cast into a desired shape which is placed in the package. The hydration gel may be cut into desired shapes. For instance, during formation of the gel, the gel may be cast on a plate and then cut into rectangles that are placed in the package. The hydration gel may also be placed in an injection member, such as a syringe or dispenser with dosing capability wherein the gel is injected into the package. The hydrogel may be cast or impregnated into a fabric or wicking material.

Prior to sterilization, the gel retains the hydration fluid so that the hydration fluid does not hydrate or substantially hydrate the hydrophilic material of the medical device. The package is then exposed to sterilizing radiation wherein the sterilizing radiation activates the gel to release the hydration fluid. For example, the hydration gel degrades upon exposure to the radiation and releases the hydration fluid. The hydration fluid then hydrates the hydrophilic material, thereby resulting in a sterilized ready to use medical product.

Referring to FIG. 1, the assembly 10, which may be a urinary or anal catheter assembly, includes an outer package 12, which may be a gas impermeable package, such as a foil package. The package 12 may define a sealed cavity that contains a device 14. The device 14, which may be a urinary or anal catheter, may be a hydrophilic catheter that may be made of a hydrophilic material or includes a hydrophilic coating on the outer surface of the shaft of the catheter. A wick 16 may also be included in the cavity of the package 12 (FIG. 2a). The wick 16 may, optionally, extend along at least a length of the device 14. As illustrated in FIG. 2a, the wick 16 may, optionally, be covered by a gas permeable, liquid impermeable barrier 18. The barrier 18 may be attached about its periphery to an inner wall of the package 12 to define a space/compartment containing the wick 16. Additionally, when the device 14 is a catheter, the shaft of catheter may be surrounded by a gas permeable non-touch sleeve 20 or may include a catheter gripping device. The wick 16 may be covered or impregnated with a gel that retains fluid. In this embodiment, after the gel releases the fluid (e.g., after exposure to sterilizing radiation), the fluid donates a gas, such as water vapor, that passes through the gas permeable, liquid impermeable barrier 18 and the no-touch sleeve 20, if these features are present. The gas hydrates the material of the device 14 so that it is ready to use. For example, water vapor hydrates the hydrophilic material of the catheter.

FIGS. 2b-2d illustrate other exemplary embodiments of the present disclosure. In FIG. 2b, the gel 22 is located in the space/compartment defined between the gas permeable, liquid impermeable barrier 18 and the internal wall of the package 12. In this embodiment, there is no wicking member and/or a no-touch sleeve, but these features could be include if desired. The gel may be injected into the space between the barrier 18 and wall of the package 12 or the gel may be a shaped piece that is placed into this space. In FIG. 2c, the gel 22 is located in the same cavity or compartment as the device 14, such as a urinary or anal catheter, such that when the gel 22 releases the liquid hydration fluid, the liquid directly contacts the hydrophilic material of the device 14 to hydrate such material. The gel may be injected into the package 12 by an injection device or the gel may be a shaped piece that is placed in the package 12. In FIG. 2d, the gel 22 is contained within a no touch sleeve surrounding at least a portion of the device 14. In one embodiment, the device may be a urinary or anal catheter having a shaft including hydrophilic material. After the gel 22 releases the liquid hydration fluid, the liquid and the device 14 are both contained within the sleeve 20a and the liquid directly contacts the material of the device 14 to hydrate the material of the device. For example, the liquid may directly contact the hydrophilic material of a catheter within the sleeve. The sleeve 20a may be a gas and liquid impermeable sleeve that contains the liquid within the sleeve.

EXAMPLES

Example I

Gel Formation

In the below described examples, a hydrogel was formed by heating water to 75° C. and then dissolving an amount of gellan gum (Kelcogel® CG-LA supplied by CP Kelco and polyethylene glycol) in the water. If an additive(s) (such as glycerol, citric acid, polyethylene glycol) was being incorporated into the hydrogel, the additive(s) was added after the gellan gum was dissolved. The mixture was allowed to cool, thereby forming a fluid releasing hydrogel.

Example II

A hydrogel including 2 wt % gellan gum and 98 wt % water was formed in the manner described above in Example I. The catheters having a hydrophilic coating on the catheter shaft along with the hydrogel were individually packaged in a vapor hydrating, gas impermeable package (such as the package of Hollister's commercial VaPro® product). In particular, such packages included a sealed gas impermeable outer foil pouch which contains the hydrophilic catheter within a cavity of the pouch. The packages also include a vapor permeable, liquid impermeable microporous barrier that is sealed, about its periphery, to an interior surface of the foil pouch. The microporous barrier was made of polyethylene impregnated with calcium carbonate. A wicking fabric was located and contained between the microporous barrier and the interior surface of the package.

During packaging of the catheters of Example II, the hydration gel was spread on the wicking fabric, which was then placed between the microporous barrier and interior surface of the pouch. The microporous barrier was then sealed to the interior surface of the pouch. The hydrophilic catheter have a no-touch gas permeable sleeve surrounding the catheter shaft (similar to that of Hollister's VaPro® commercial product) was placed into the cavity of the foil pouch and the pouch was sealed. The packages were then exposed to gamma radiation at a dose of between about 25 kGy and about 45 kGy. The packages were stored for five days.

After storage, the packages were opened, the catheters were removed and the coefficients of friction of the catheters were measured. In particular, the the initial, abraded and ten minute dry-out coefficients of friction (CoFs) of each of the catheters was measured with the hydrophilic coating in a hydrated state.

The CoF measurements are an indicator of lubricity and were measured using a Harland Friction Tester Model FTS5500. The CoFs of the catheters were determined by inserting a mandrel into 127 mm section of the coated catheter tube. The tube was then clamped between two pieces of silicone rubber at 100 g load wherein the silicone rubber had a shore hardness of 60 A. The catheter tube with the mandrel inserted therein was pulled through the two pieces of silicone rubber at a speed of 10 mm/s. The force required to pull about 80 mm of the catheter tube through the two pieces of silicone rubber was measured. The CoF value was calculated from the ratio of recorded to applied loads (i.e., the recorded load divided by the applied load) when steady state was reached. The CoF of each catheter was measured immediately after removal from the package ("initial"), immediately after being abraded ("abraded") and immediately after a ten-minute dry-out time ("dry-out").

In measuring the abraded CoFs, the catheter, with the hydrophilic coating in a hydrated state, was cycled back and forth 25 times through a hole in a 1 mm thick, silicone pad having a shore hardness of 60 A. The hole about 90% of the diameter than the outer diameter of the catheter tube and the abrasion took place under water. Abrading the catheter in this fashion is designed to remove any portions of the coating that is not well adhered to the tubes. After abrasion, the CoF was measured as described above.

In measuring the ten minute dry-out time CoF, the catheter was removed from the package and was placed in an atmosphere having a temperature of 23° C. and a relative humidity of 50% for 10 minutes before measuring the CoF as described above.

Dye uptake tests also were conducted on the catheters to assess the level of adhesion/non-adhesion between the hydrophilic coatings and catheters. After the CoFs of the "abraded" and "dry out" catheters were measured, the catheters were dehydrated. The dehydrated catheters were then immersed in a water soluble red dye for 2 minutes. The catheters were then visually inspected to determine if the dye had been uniformly taken up throughout the coating or if sections of the coated portion of the catheter were dye-free. A uniform dye uptake throughout the coated portion of the catheter indicates that the hydrophilic coating has good adhesion to the catheter and is indicated as "pass" in the result tables below. If the coated portion of the catheter has undyed sections, this is an indication that the hydrophilic coating or sections thereof have significantly thinned and/or separated from the catheter due to lack of adhesion to the catheter.

Table 1 lists the initial and abraded CoF measurements and the results of the dye test of the abraded catheter samples.

TABLE 1

| Sample | Initial COF | Abrasion COF | Abraded Dye Test |
|---|---|---|---|
| 2-1 | 0.016 | 0.011 | Pass |
| 2-2 | 0.020 | 0.018 | Pass |
| 2-3 | 0.017 | 0.014 | Pass |
| 2-4 | 0.018 | 0.006 | Pass |
| 2-5 | 0.019 | 0.010 | Pass |
| 2-6 | 0.016 | 0.017 | Pass |
| 2-7 | 0.014 | 0.008 | Pass |
| 2-8 | 0.011 | 0.009 | Pass |
| Average | 0.016 | 0.011 | |
| Std. Dev. | 0.003 | 0.004 | |

Table 2 lists the dry out CoF measurements and the results of the dye test after the dry out CoFs were measured for the catheter samples.

TABLE 2

| Sample | 10 Min Dry Out COF | Dry Out Sample Dye Test |
|---|---|---|
| 2-9 | 0.025 | Pass |
| 2-10 | 0.026 | Pass |
| 2-11 | 0.028 | Pass |
| 2-12 | 0.028 | Pass |
| 2-13 | 0.025 | Pass |
| 2-14 | 0.026 | Pass |
| 2-15 | 0.029 | Pass |
| 2-16 | 0.027 | Pass |
| Average | 0.027 | |
| Std. Dev. | 0.002 | |

Example III

A hydrogel including 2 wt % gellan gum and 98 wt % water was formed in the manner described above in Example I. The catheters having a hydrophilic coating on the catheter shaft were individually packaged with the hydrogel spread on the fabric of a vapor hydrating, gas impermeable package, as described above in Example II. In this example, the catheter did not include a no-touch sleeve. The packages were exposed to gamma radiation and stored, as described above in Example II. The initial, abraded and dry-out CoFs were measured and dye uptake tests were conduct in the same manner as described in Example II.

Table 3 lists the initial and abraded CoF measurements and the results of the dye test of the abraded catheter samples.

TABLE 3

| Sample | Initial COF | Abrasion COF | Abraded Dye test |
|---|---|---|---|
| 3-1 | 0.015 | 0.010 | Pass |
| 3-2 | 0.021 | 0.070 | Pass |
| 3-3 | 0.020 | 0.010 | Pass |
| 3-4 | 0.014 | 0.027 | Pass |
| 3-5 | 0.017 | 0.013 | Pass |
| 3-6 | 0.037 | 0.010 | Pass |
| 3-7 | 0.018 | 0.023 | Pass |
| 3-8 | 0.011 | 0.006 | Pass |
| Average | 0.019 | 0.021 | |
| Std. Dev. | 0.008 | 0.021 | |

Table 4 lists the dry out CoF measurements and the results of the dye test after the dry out CoFs were measured for the catheter samples.

TABLE 4

| Sample | 10 Min Dry Out COF | Dry Out Sample Dye Test |
|---|---|---|
| 3-9 | 0.025 | Pass |
| 3-10 | 0.010 | Pass |
| 3-11 | 0.026 | Pass |
| 3-12 | 0.011 | Pass |
| 3-13 | 0.026 | Pass |
| 3-14 | 0.023 | Pass |
| 3-15 | 0.024 | Pass |
| 3-16 | 0.027 | Pass |
| Average | 0.022 | |
| Std. Dev. | 0.007 | |

Example IV

A hydrogel including 2 wt % gellan gum and 98 wt % water was formed in the manner described above in Example I. The catheters having a hydrophilic coating on the catheter shaft and a no-touch sleeve surrounding the catheter shaft were individually packaged with the hydrogel in a vapor hydrating, gas impermeable package, as described above in Example II, except that the package did not contain a wicking fabric in the space between the microporous barrier and the interior surface of the pouch. Instead, the hydrogel was placed in a syringe and injected between the microporous barrier and the interior surface of the pouch. The packages were exposed to gamma radiation and stored, as described above in Example II. The initial, abraded and dry-out CoFs were measured and dye uptake tests were conduct in the same manner as described in Example II.

Table 5 lists the initial and abraded CoF measurements and the results of the dye test of the abraded catheter samples.

TABLE 5

| Sample | Initial COF | Abrasion COF | Abraded Dye test |
|---|---|---|---|
| 4-1 | 0.016 | 0.013 | Pass |
| 4-2 | 0.017 | 0.018 | Pass |
| 4-3 | 0.017 | 0.007 | Pass |
| 4-4 | 0.022 | 0.007 | Pass |
| 4-5 | 0.016 | 0.008 | Pass |
| 4-6 | 0.010 | 0.007 | Pass |
| 4-7 | 0.012 | 0.016 | Pass |
| 4-8 | / | / | Pass |
| Average | 0.016 | 0.011 | |
| Std. Dev. | 0.004 | 0.005 | |

Table 6 lists the dry out CoF measurements and the results of the dye test after the dry out CoFs were measured for the catheter samples.

TABLE 6

| Sample | 10 Min Dry Out COF | Dried Dye test |
|---|---|---|
| 4-9 | 0.027 | Pass |
| 4-10 | 0.029 | Pass |
| 4-11 | 0.028 | Pass |
| 4-12 | 0.025 | Pass |
| 4-13 | 0.024 | Pass |
| 4-14 | 0.025 | Pass |
| 4-15 | 0.027 | Pass |
| 4-16 | / | Pass |
| Average | 0.026 | |
| Std. Dev. | 0.002 | |

Example V

A hydrogel including 2 wt % gellan gum and 98 wt % water was formed in the manner described above in Example I. The catheters having a hydrophilic coating on the catheter shaft were individually packaged with the hydrogel in a vapor hydrating, gas impermeable package, as described above in Example II, except that the package did not contain a wicking fabric in the space between the microporous barrier and the interior surface of the pouch. Instead, the hydrogel was placed in a syringe and injected between the microporous barrier and the interior surface of the pouch. In this example, the catheters did not include a no-touch sleeve. The packages were exposed to gamma radiation and stored, as described above in Example II. The initial, abraded and dry-out CoFs were measured and dye uptake tests were conduct in the same manner as described in Example II.

Table 7 lists the initial and abraded CoF measurements and the results of the dye test of the abraded catheter samples.

TABLE 7

| Sample | Initial COF | Abrasion COF | Abraded Dye test |
|---|---|---|---|
| 5-1 | 0.016 | 0.011 | Pass |
| 5-2 | 0.019 | 0.018 | Pass |
| 5-3 | 0.016 | 0.007 | Pass |
| 5-4 | 0.015 | 0.008 | Pass |
| 5-5 | 0.018 | 0.012 | Pass |
| 5-6 | 0.025 | 0.011 | Pass |
| 5-7 | 0.018 | 0.010 | Pass |
| 5-8 | 0.017 | 0.028 | Pass |
| Average | 0.018 | 0.013 | |
| Std. Dev. | 0.003 | 0.007 | |

Table 8 lists the dry out CoF measurements and the results of the dye test after the dry out CoFs were measured for the catheter samples.

TABLE 8

| Sample | 10 Min Dry Out COF | Dried Dye test |
|---|---|---|
| 5-9 | 0.018 | Pass |
| 5-10 | 0.022 | Pass |
| 5-11 | 0.027 | Pass |
| 5-12 | 0.030 | Pass |
| 5-13 | 0.029 | Pass |
| 5-14 | 0.027 | Pass |
| 5-15 | 0.026 | Pass |
| 5-16 | 0.031 | Pass |
| Average | 0.026 | |
| Std. Dev. | 0.004 | |

Example VI

A hydrogel including 1.5 wt % gellan gum, 0.1 wt % citric acid and 98.4 wt % water was formed in the manner described above in Example I. The catheters having a hydrophilic coating on the catheter shaft and a gas permeable no-touch sleeve surrounding the catheter shaft were individually packaged with the hydrogel in a vapor hydrating, gas impermeable package, as described above in Example IV (no wicking fabric). The packages were exposed to gamma radiation and stored, as described above in Example II. The initial, abraded and dry-out CoFs were measured and dye uptake tests were conduct in the same manner as described in Example II.

Table 9 lists the initial and abraded CoF measurements and the results of the dye test of the abraded catheter samples.

TABLE 9

| Sample | Initial COF | Abrasion COF | Abraded Dye test |
|---|---|---|---|
| 6-1 | 0.017 | 0.015 | Pass |
| 6-2 | 0.017 | 0.079 | Pass |
| 6-3 | 0.013 | 0.008 | Pass |
| 6-4 | 0.016 | 0.006 | Pass |
| 6-5 | 0.013 | 0.007 | Pass |
| 6-6 | 0.015 | 0.008 | Pass |
| 6-7 | 0.012 | 0.006 | Pass |
| 6-8 | 0.015 | 0.008 | Pass |
| Average | 0.015 | 0.017 | |
| Std. Dev. | 0.002 | 0.025 | |

Table 10 lists the dry out CoF measurements and the results of the dye test after the dry out CoFs were measured for the catheter samples. Table 10

TABLE 10

| Sample | 10 Min Dry Out COF | Dried Dye test |
|---|---|---|
| 6-9 | 0.023 | Pass |
| 6-10 | 0.025 | Pass |
| 6-11 | 0.025 | Pass |
| 6-12 | 0.028 | Pass |
| 6-13 | 0.025 | Pass |
| 6-14 | 0.024 | Pass |
| 6-15 | 0.026 | Pass |
| 6-16 | 0.023 | Pass |
| Average | 0.025 | |
| Std. Dev. | 0.002 | |

Example VII

A hydrogel including 1.5 wt % gellan gum, 0.1 wt % citric acid and 98.4 wt % water was formed in the manner described above in Example I. The catheters having a hydrophilic coating on the catheter shaft were individually packaged with the hydrogel in a vapor hydrating, gas impermeable package, as described above in Example IV (no wicking fabric). In this example, the catheter did not include a no-touch sleeve. The packages were exposed to gamma radiation and stored, as described above in Example II. The initial, abraded and dry-out CoFs were measured and dye uptake tests were conduct in the same manner as described in Example II.

Table 11 lists the initial and abraded CoF measurements and the results of the dye test of the abraded catheter samples.

TABLE 11

| Sample | Initial COF | Abrasion COF | Abraded Dye test |
| --- | --- | --- | --- |
| 7-1 | 0.015 | 0.006 | Pass |
| 7-2 | 0.013 | 0.008 | Pass |
| 7-3 | 0.018 | 0.015 | Pass |
| 7-4 | 0.014 | 0.085 | Pass |
| 7-5 | 0.019 | 0.016 | Pass |
| 7-6 | 0.019 | 0.008 | Pass |
| 7-7 | 0.014 | 0.013 | Pass |
| 7-8 | 0.017 | 0.027 | Pass |
| Average | 0.016 | 0.022 | |
| Std. Dev. | 0.003 | 0.026 | |

Table 12 lists the dry out CoF measurements and the results of the dye test after the dry out CoFs were measured for the catheter samples.

TABLE 12

| Sample | 10 Min Dry Out COF | Dried Dye test |
| --- | --- | --- |
| 7-9 | 0.019 | Pass |
| 7-10 | 0.020 | Pass |
| 7-11 | 0.014 | Pass |
| 7-12 | 0.024 | Pass |
| 7-13 | 0.019 | Pass |
| 7-14 | 0.017 | Pass |
| 7-15 | 0.017 | Pass |
| 7-16 | 0.029 | Pass |
| Average | 0.020 | |
| Std. Dev. | 0.005 | |

Example VIII

A hydrogel including 1.375 wt % gellan gum, 0.375 wt % glycerol and 98.25 wt % was formed in the manner described above in Example I. The catheters having a hydrophilic coating on the catheter shaft and a no-touch sleeve covering the catheter shaft were individually packaged with the hydrogel in a gas impermeable foil package. In particular, the catheter and hydrogel were placed in the cavity of the gas impermeable foil package and the foil package was sealed. There was no barrier between the catheter and the hydrogel within the cavity.

The packages were then exposed to gamma radiation at a dose of between about 25 kGy and about 45 kGy. The packages were stored for five days. The initial, abraded and dry-out CoFs were measured and dye uptake tests were conducted in the same manner as described in Example II.

Table 13 lists the initial and abraded CoF measurements and the results of the dye test of the abraded catheter samples.

TABLE 13

| Sample | Initial COF | Abrasion COF | Abraded Dye test |
| --- | --- | --- | --- |
| 8-1 | 0.012 | 0.006 | Pass |
| 8-2 | 0.016 | 0.006 | Pass |
| 8-3 | 0.022 | 0.015 | Pass |
| 8-4 | 0.021 | 0.003 | Pass |
| 8-5 | 0.014 | 0.012 | Pass |
| 8-6 | 0.014 | 0.016 | Pass |
| 8-7 | 0.013 | 0.023 | Pass |
| 8-8 | 0.014 | 0.013 | Pass |
| Average | 0.016 | 0.012 | |
| Std. Dev. | 0.004 | 0.006 | |

Table 14 lists the dry out CoF measurements and the results of the dye test after the dry out CoFs were measured for the catheter samples.

TABLE 14

| Sample | 10 Min Dry Out COF | Dried Dye test |
| --- | --- | --- |
| 8-9 | 0.016 | Pass |
| 8-10 | 0.025 | Pass |
| 8-11 | 0.022 | Pass |
| 8-12 | 0.020 | Pass |
| 8-13 | 0.019 | Pass |
| 8-14 | 0.061 | Pass |
| 8-15 | 0.021 | Pass |
| 8-16 | 0.020 | Pass |
| Average | 0.025 | |
| Std. Dev. | 0.015 | |

Example IX

A hydrogel including 1.375 wt % gellan gum, 0.375 wt % glycerol and 98.25 wt % water was formed in the manner described above in Example I. The catheters having a hydrophilic coating on the catheter shaft were individually packaged with the hydrogel in a gas impermeable foil package. In particular, the catheter and hydrogel were placed in the cavity of the gas impermeable foil package and the foil package was sealed. There was no barrier between the catheter and the hydrogel within the cavity. Also, the catheter did not include a no-touch sleeve.

The packages were then exposed to gamma radiation at a dose of between about 25 kGy and about 45 kGy. The packages were stored for five days. The initial, abraded and dry-out CoFs were measured and dye uptake tests were conducted in the same manner as described in Example II.

Table 15 lists the initial and abraded CoF measurements and the results of the dye test of the abraded catheter samples.

TABLE 15

| Sample | Initial COF | Abrasion COF | Abraded Dye test |
| --- | --- | --- | --- |
| 9-1 | 0.020 | 0.018 | Pass |
| 9-2 | 0.022 | 0.016 | Pass |
| 9-3 | 0.020 | 0.029 | Pass |
| 9-4 | 0.022 | 0.020 | Pass |
| 9-5 | 0.022 | 0.013 | Pass |

TABLE 15-continued

| Sample | Initial COF | Abrasion COF | Abraded Dye test |
|---|---|---|---|
| 9-6 | 0.020 | 0.023 | Pass |
| 9-7 | 0.018 | 0.017 | Pass |
| 9-8 | 0.015 | 0.019 | Pass |
| Average | 0.020 | 0.019 | |
| Std. Dev. | 0.002 | 0.005 | |

Table 16 lists the dry out CoF measurements and the results of the dye test after the dry out CoFs were measured for the catheter samples.

TABLE 16

| Sample | 10 Min Dry Out COF | Dried Dye test |
|---|---|---|
| 9-9 | 0.028 | Pass |
| 9-10 | 0.026 | Pass |
| 9-11 | 0.027 | Pass |
| 9-12 | 0.025 | Pass |
| 9-13 | 0.029 | Pass |
| 9-14 | 0.019 | Pass |
| 9-15 | 0.019 | Pass |
| 9-16 | 0.030 | Pass |
| Average | 0.025 | |
| Std. Dev. | 0.004 | |

Example X

In this example, a hydrogels were formed from the below listed compositions in the manner described in Example 1. Each of the hydrogels was individually placed in a pouch and the pouch was sealed. The pouches were then exposed to gamma radiation at a dose of about 25 kGy to about 40 kGy. After being exposed to radiation, the packages were opened and the consistency of the contents (hydrogel) was visual observed to determine if the gel transitioned into a liquid, remained a gel or was a semi-solid (partially a gel and some liquid). Any liquid within the package was then placed on both a white piece of fabric and a black piece of fabric. The fabric was allowed to dry and a visual inspection of the fabric was conducted to determine if any staining occurred.

Table 17 lists the results of this example.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A radiation sterilized catheter assembly, comprising:
   a gas impermeable package defining a sealed cavity;
   a urinary catheter or anal catheter within the sealed cavity, the urinary or anal catheter comprising a hydrophilic coating;
   a radiation activated liquid releasing hydrogel including a hydration liquid and between 0.1 wt % and 5 wt % of gellan gum, the radiation activated liquid releasing hydrogel located within the sealed cavity and releasing the hydration liquid upon exposure to radiation, the released hydration liquid hydrating the hydrophilic coating; and
   the hydration liquid fluid comprising an anti-staining additive.

2. The assembly of claim 1 wherein the hydration liquid comprises water.

3. The assembly of claim 1 wherein the hydration liquid comprises another additive.

4. The assembly of claim 1 wherein the radiation activated liquid releasing hydrogel degrades upon exposure to radiation, thereby releasing the hydration liquid.

5. The assembly of claim 1 wherein the urinary catheter includes a shaft and at least the catheter shaft is surrounded by a sleeve, and the catheter shaft and radiation activated liquid releasing hydrogel are contained within the sleeve.

6. The assembly of claim 1 further comprising a package wherein the urinary or anal catheter and radiation activated liquid releasing hydrogel are located within the package.

7. The assembly of claim 1 wherein the radiation activated liquid releasing hydrogel is in contact with the urinary catheter or anal catheter.

TABLE 17

| Sample | Gellan Gum wt % | Glycerol wt % | Citric Acid wt % | Polyethylene Glycol wt % | Consistency of Contents | White Fabric | Black Fabric |
|---|---|---|---|---|---|---|---|
| 10-1 | 2.0 | 0 | 0 | 0 | Liquid | Yellow Stain | No Noticeable Stain |
| 10-2 | 1.5 | 0 | 0 | 0 | Liquid | Yellow Stain | No Noticeable Stain |
| 10-3 | 1.5 | 0.5 | 0 | 0 | Liquid | No Noticeable Stain | Fragments of White Deposit |
| 10-4 | 1.25 | 0 | 0 | 0 | Liquid | Yellow Stain | No Noticeable Stain |
| 10-5 | 1.25 | 0.5 | 0 | 0 | Liquid | No Noticeable Stain | No Noticeable Stain |
| 10-6 | 1.25 | 1 | 0 | 0 | Liquid | Fragments of White Deposit | Transparent Film Formed |
| 10-7 | 1.25 | 0.5 | 0.05 | | Liquid | No Noticeable Stain | Transparent Film Formed |
| 10-8 | 1.25 | 0.5 | 0.1 | | Semi-solid | Transparent Film Formed | Transparent Film Formed |
| 10-9 | 1 | 0 | 0 | 0 | Liquid | Yellow Stain | No Noticeable Stain |
| 10-10 | 1 | 0.5 | 0 | 0 | Liquid | No Noticeable Stain | No Noticeable Stain |
| 10-11 | 1 | 1 | 0 | 0 | Semi-solid | No Noticeable Stain | Fragments of White Deposit |
| 10-12 | 1 | 0 | 0 | 0.5 | Liquid | Fragments of White Deposit | Transparent Film Formed |
| 10-13 | 1 | 0 | 0 | 1.0 | Liquid | Fragments of White Deposit | Transparent Film Formed |

8. The assembly of claim 1 wherein the radiation activated liquid releasing hydrogel at least partially covers the urinary catheter or anal catheter.

9. The assembly of claim 1 wherein the radiation activated liquid releasing hydrogel is separated from the urinary catheter or anal catheter.

10. The assembly of claim 1 wherein the radiation activated liquid releasing hydrogel and the urinary catheter or anal catheter are unconfined within a package.

11. The assembly of claim 1 wherein a concentration of the hydration liquid in the radiation activated liquid releasing hydrogel comprises about 40 wt % and 99.8 wt %.

12. The assembly of claim 1 wherein a concentration of the hydration liquid in the radiation activated liquid releasing hydrogel comprises 98 wt %.

13. The assembly of claim 1 wherein the anti-staining additive comprises one or more of polyols, polyethers and carboxylic acid.

14. The assembly of claim 1 wherein the anti-staining additive comprises one or more of glycerol, polyethylene glycol and citric acid.

15. The assembly of claim 1 wherein the anti-staining additive is between about 0.1 wt % and about 2 wt % of the hydration liquid fluid.

16. A radiation sterilized catheter assembly, comprising:
a gas impermeable package defining a sealed cavity;
a urinary catheter or anal catheter within the sealed cavity, the urinary or anal catheter comprising a hydrophilic coating; and
a radiation activated liquid releasing hydrogel including a hydration liquid and between 0.1 wt % and 5 wt % of gellan gum, the radiation activated liquid releasing hydrogel located within the sealed cavity and releasing the hydration liquid upon exposure to radiation, the released hydration liquid hydrating the hydrophilic coating.

17. The assembly of claim 16 wherein the hydration liquid comprises water.

18. The assembly of claim 16 wherein the hydration liquid comprises another additive.

19. The assembly of claim 16 wherein the radiation activated liquid releasing hydrogel degrades upon exposure to radiation, thereby releasing the hydration liquid.

20. The assembly of claim 16 wherein the urinary or anal catheter includes a shaft and at least the catheter shaft is surrounded by a sleeve, and the catheter shaft and radiation activated liquid releasing hydrogel are contained within the sleeve.

21. The assembly of claim 16 further comprising a package wherein the urinary or anal catheter and radiation activated liquid releasing hydrogel are located within the package.

22. The assembly of claim 16 wherein the radiation activated liquid releasing hydrogel is in contact with the urinary catheter or anal catheter.

23. The assembly of claim 16 wherein the radiation activated liquid releasing hydrogel at least partially covers the urinary catheter or anal catheter.

24. The assembly of claim 16 wherein the radiation activated liquid releasing hydrogel is separated from the urinary catheter or anal catheter.

25. The assembly of claim 16 wherein the radiation activated liquid releasing hydrogel and the urinary catheter or anal catheter are unconfined within a package.

26. The assembly of claim 16 wherein a concentration of the hydration liquid in the radiation activated liquid releasing hydrogel comprises about 40 wt% and 99.8 wt%.

27. The assembly of claim 16 wherein a concentration of the hydration liquid in the radiation activated liquid releasing hydrogel comprises 98 wt%.

* * * * *